United States Patent
Bland et al.

(10) Patent No.: US 9,000,180 B2
(45) Date of Patent: Apr. 7, 2015

(54) PROCESSES FOR THE PRODUCTION OF N-SUBSTITUTED SULFOXIMINE PYRIDINE N-OXIDES

(71) Applicant: Dow AgroSciences LLC, Indianapolis, IN (US)

(72) Inventors: Douglas C. Bland, Midland, MI (US); Ronald Ross, Jr., Zionsville, IN (US); Peter L. Johnson, Indianapolis, IN (US); Timothy C. Johnson, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/921,288

(22) Filed: Jun. 19, 2013

(65) Prior Publication Data
US 2014/0005406 A1    Jan. 2, 2014

Related U.S. Application Data

(60) Provisional application No. 61/666,807, filed on Jun. 30, 2012, provisional application No. 61/666,808, filed on Jun. 30, 2012.

(51) Int. Cl.
C07D 211/92    (2006.01)
C07D 213/89    (2006.01)
C07D 409/04    (2006.01)

(52) U.S. Cl.
CPC ............ *C07D 213/89* (2013.01); *C07D 409/04* (2013.01)

(58) Field of Classification Search
CPC .................................................. C07D 213/20
See application file for complete search history.

(56) References Cited

U.S. PATENT DOCUMENTS

| | | | |
|---|---|---|---|
| 4,050,921 | A | 9/1977 | Plant et al. |
| 4,212,870 | A | 7/1980 | Gibbs |
| 7,511,149 | B2 | 3/2009 | Arndt et al. |
| 7,678,920 | B2 | 3/2010 | Zhu et al. |
| 7,687,634 | B2 | 3/2010 | Loso et al. |
| 8,188,292 | B2 | 5/2012 | Loso et al. |
| 8,193,222 | B1 | 6/2012 | Bland et al. |
| 2008/0033180 | A1 | 2/2008 | Renga et al. |
| 2008/0207910 | A1 | 8/2008 | Podhorez et al. |
| 2009/0221424 | A1 | 9/2009 | Breaux et al. |
| 2010/0004457 | A1 | 1/2010 | Bland et al. |
| 2010/0168178 | A1 | 7/2010 | Qin et al. |
| 2012/0122681 | A1 | 5/2012 | Le Vezouet et al. |

FOREIGN PATENT DOCUMENTS

| | | |
|---|---|---|
| EP | 2170066 B1 | 2/2012 |
| WO | 2010002577 | 1/2010 |
| WO | 2012084858 A2 | 6/2012 |

OTHER PUBLICATIONS

Davies, IW, et al., "A practical, efficient, and rapid method for the oxidation of electron deficient pyridines using trifluoroacetic anhydride and hydrogen peroxide-urea complex", Tetrahedron Letters, 2000, pp. 2299-2302; abstract; pp. 2300-2301, table 3, compound 5, vol. 41, Groton, CT.
International Search Report dated Nov. 26, 2013 from application No. PCT/US2013/45300.
International Search Report dated Nov. 22, 2013 from application No. PCT/US2013/45333.
International Search Report dated Nov. 22, 2013 from application No. PCT/US2013/045556.
Non-Final Office Action dated Nov. 22, 2013 from U.S. Appl. No. 13/917,030.
U.S. Appl. No. 13/917,030, filed Jun. 13, 2013.
U.S. Appl. No. 13/919,035, filed Jun. 17, 2013.
Caron, et al.; A practical, efficient, and rapid method for the oxidation of electron deficient pyridines using trifluoroacetic anhydride and hydrogen peroxide-urea complex; Tetrahedron Letters 41 (2000) 2299-2302.
Chung et al.; Synthesis of 3-Aminopyrazinone Mediated by 2-Pyridylthioimidate-ZnCl2 Complexes, Development of an Efficient Route to a Thrombin Inhibitor; J. Org. Chem 2003, 68, 8838-8846.
Degraw et al., "An Alternate Synthesis of 6-Substituted-5-deazapteridines"; Journal of Heterocyclic Chemistry, vol. 19 (1982), pp. 1461-1463.
Albini et al., Heterocyclic N-oxides, CRC Press, (1991), Chapter 2, pp. 7-29.
Prikhod'ko et al., "Cyclization of Oximes of 3-formyl-2-acetylenylindole"; Bulletin of the Academy of Sciences of the USSR Division of Chemical Science, vol. 33 (1984), pp. 2383-2385.

*Primary Examiner* — Heidi Reese
(74) *Attorney, Agent, or Firm* — Carl D. Corvin; Maschoff Brennan

(57) ABSTRACT

In one form, processes for the production of certain N-substituted sulfoximine N-oxides are provided. Further embodiments, forms, objects, features, advantages, aspects, and benefits shall become apparent from the description.

10 Claims, No Drawings

PROCESSES FOR THE PRODUCTION OF N-SUBSTITUTED SULFOXIMINE PYRIDINE N-OXIDES

CROSS-REFERENCE TO RELATED APPLICATIONS

The present application claims priority to U.S. Provisional Patent Application No. 61/666,807 filed Jun. 30, 2012, the content of which is incorporated herein by reference in its entirety, and U.S. Provisional Patent Application No. 61/666,808 filed Jun. 30, 2012, the content of which is incorporated herein by reference in its entirety.

FIELD OF THE INVENTION

The invention disclosed in this document is related to the field of processes to produce certain N-substituted sulfoximine pyridine N-oxides.

BACKGROUND OF THE INVENTION

Controlling pest populations is essential to modern agriculture, food storage, and hygiene. There are more than ten thousand species of pests that cause losses in agriculture. The world-wide agricultural losses amount to billions of U.S. dollars each year. Pests, such as termites, are also known to cause damage to all kinds of private and public structures resulting in billions of U.S. dollars in losses each year. Pests also eat and adulterate stored food, resulting in billions of U.S. dollars in losses each year, as well as deprivation of food needed for people.

Certain pests have or are developing resistance to pesticides in current use. Hundreds of pest species are resistant to one or more pesticides. Accordingly, there exists a continuous need for new pesticides and for processes of forming such pesticides.

U.S. Pat. Nos. 7,678,920 and 7,687,634 describe certain pesticidal sulfoximine compounds including some containing a pyridine functional group. It has now been surprisingly discovered that forms of one or more of these compounds where the pyridine functional group has been N-oxidized exhibit pesticidal properties. Pyridine N-oxides are commonly prepared from direct oxidation with peracids, such as m-chloroperoxybenzoic acid (MCPBA). In the current instance however, it has been observed that attempts to directly oxidize certain sulfoximine compounds having a pyridine functional group with MCPBA do not yield the desired N-oxidized product. Accordingly, there exists a need for processes of forming such N-oxidized compounds.

DETAILED DESCRIPTION

For purposes of promoting an understanding of the principles of the invention, reference will now be made to the following embodiments and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Unless specifically limited otherwise, the term alkyl (including derivative terms such as alkoxy) as used herein includes straight chain, branched chain, and cyclic groups. Thus, typical alkyl groups are methyl, ethyl, 1-methylethyl, propyl, 1,1-dimethylethyl, and cyclopropyl. The term halogen includes fluorine, chlorine, bromine, and iodine.

The compounds disclosed herein can exist as one or more stereoisomers. The various stereoisomers include geometric isomers, diastereomers and enantiomers. Thus, the compounds disclosed in this document may include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

In one embodiment, a process is provided for preparing pyridine N-oxidized sulfoximine compounds of the formula (I)

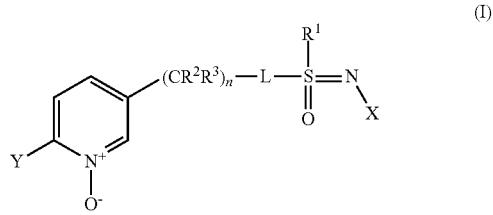

wherein
X represents $NO_2$, CN, $COOR^4$ or $CONH_2$;
L represents a single bond or $R^1$, S and L taken together represent a 4-, 5- or 6-membered ring;
$R^1$ represents $(C_1-C_4)$ alkyl;
$R^2$ and $R^3$ individually represent hydrogen, methyl, ethyl, flouro, chloro or bromo;
n is an integer from 0-3;
Y represents $(C_1-C_4)$ haloalkyl, F, Cl, Br, or I; and
$R^4$ represents $(C_1-C_3)$ alkyl.

More particular but non-limiting forms of compounds of formula (I) include the following classes:

(1) Compounds of formula (I) wherein X is $NO_2$, CN or $CONH_2$.
(2) Compounds of formula (I) wherein Y is $CF_3$ or Cl.
(3) Compounds of formula (I) wherein $R^2$ and $R^3$ independently represent hydrogen, methyl or ethyl.
(4) Compounds of formula (I) wherein $R^1$ represents $CH_3$ and L represents a single bond, i.e., having the structure

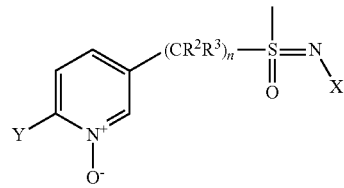

wherein n=1-3.
(5) Compounds of formula (I) wherein $R^1$, S and L taken together form a saturated 5-membered ring and n is 0, i.e., having the structure

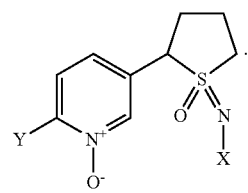

It will be appreciated by those skilled in the art that one or more combinations of the above described classes of the compound of formula (I) are possible and fall within the scope of this document.

In one aspect, the process for preparing N-oxidized sulfoximine compounds of the formula (I) wherein X, L, $R^1$, $R^2$, $R^3$, n, Y and $R^4$ are as previously defined includes an oxidation of compounds according to the formula (II)

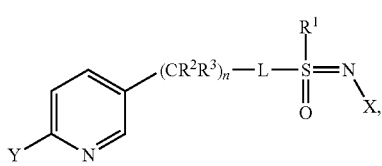

(II)

wherein X, L, $R^1$, $R^2$, $R^3$, n, Y and $R^4$ are as previously defined, by the addition of urea hydrogen peroxide and trifluoroacetic anhydride according to the following reaction scheme:

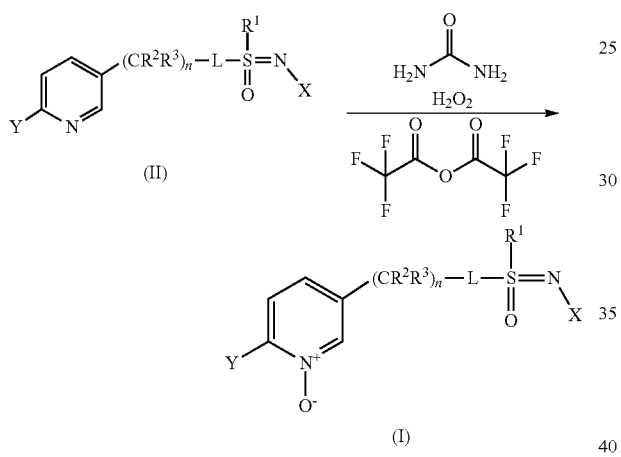

In one form, the oxidation is conducted at a temperature from about 0° C. to about 30° C. In another exemplary form, the oxidation can be carried out at room temperature and ambient pressure, but the use of higher or lower temperatures and pressures, if desired, is contemplated.

Non-limiting examples of solvents which can be used include polar solvents such as dichloromethane, tetrahydrofuran, ethyl acetate, acetone, dimethylformamide, acetonitrile, and dimethyl sulfoxide.

In one form, the compound of formula (II) is mixed with urea hydrogen peroxide and the solvent and stirred. Trifluoroacetic anhydride is then added to the resultant mixture followed by additional stirring until all or a major portion of the starting materials have been consumed. The reaction mixture may then be filtered, washed and concentrated in vacuo. The remaining residue is then taken up in a suitable solvent, such as THF (tetrahydrofuran), and washed, and the organic phase is dried, filtered and concentrated in vacuo to provide the respective compound according to Formula (I). It should be appreciated however that the foregoing steps are not limiting, and that variations and additions to the same are possible and contemplated.

Further details regarding the preparation of compounds of formula (II) wherein X is $NO_2$, CN, or $COOR^4$ and L, $R^1$, $R^2$, $R^3$, n, Y and $R^4$ are as previously defined are found in U.S. Pat. Nos. 7,678,920 and 7,687,634. The contents of these references are hereby incorporated herein by reference in their entirety. Preparation of compounds of formula (II) wherein X is $CONH_2$ and L, $R^1$, $R^2$, $R^3$, n, Y and $R^4$ are as previously defined may be accomplished, for example, by producing a compound of formula (II) wherein X is CN and L, $R^1$, $R^2$, $R^3$, n, Y and $R^4$ are as previously defined, i.e., having the following structure

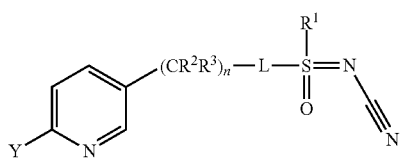

and subjecting it to an acid hydrolysis reaction. Non-limiting examples of acids that may be used in this reaction include sulfuric acid, hydrochloric acid, phosphoric acid, trifluoroacetic acid, and nitric acid.

In one form, the acid hydrolysis reaction is conducted at a temperature from about 50° C. to about 90° C. and at ambient pressure, but the use of higher or lower temperatures and pressures, if desired, is contemplated.

Non-limiting examples of solvents which can be used in the acid hydrolysis reaction include polar solvents such as dichloromethane, tetrahydrofuran, ethyl acetate, acetone, dimethylformamide, acetonitrile, and dimethyl sulfoxide.

As an alternative approach, the preparation of N-oxidized sulfoximine compounds of the formula (I) wherein X is $CONH_2$ and L, $R^1$, $R^2$, $R^3$, n, Y and $R^4$ are as previously defined may be accomplished, for example, by producing a compound of formula (I) pursuant to the oxidation process outlined above wherein X is CN and L, $R^1$, $R^2$, $R^3$, n, Y and $R^4$ are as previously defined, i.e., having the following structure

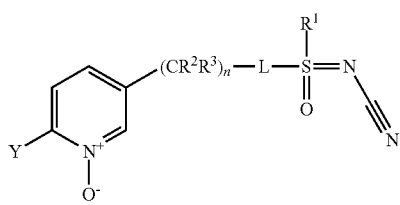

and subjecting it to an acid hydrolysis reaction. Non-limiting examples of acids that may be used in this reaction include sulfuric acid, hydrochloric acid, phosphoric acid, trifluoroacetic acid, and nitric acid.

In one form, the acid hydrolysis reaction is conducted at a temperature from about 50° C. to about 90° C. and at ambient pressure, but the use of higher or lower temperatures and pressures, if desired, is contemplated.

Non-limiting examples of solvents which can be used in the acid hydrolysis reaction include polar solvents such as dichloromethane, tetrahydrofuran, ethyl acetate, acetone, dimethylformamide, acetonitrile, and dimethyl sulfoxide.

EXAMPLES

The following examples are for illustration purposes and are not to be construed as limiting the invention disclosed in this document to only the embodiments disclosed in these examples.

Starting materials, reagents and solvents which were obtained from commercial sources were used without further purification. Molecules are given their known names, named according to naming programs within ISIS Draw, ChemDraw or ACD Name Pro. If such programs are unable to name a molecule, the molecule is named using conventional naming rules.

Example 1

Preparation of [methyl(oxido){1-1-oxido-6-(trifluoromethyl)pyridin-3-yl]ethyl}-λ⁶-sulfanylidene] cyanamide (1)

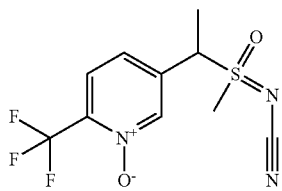

(1)

Trifluoroacetic anhydride (TFAA) was added dropwise to a mixture of {1-[6-(trifluoromethyl)pyridin-3-yl]ethyl}(methyl)oxido-λ⁴-sulfanylidenecyanamide (2) and urea hydrogen peroxide in 10 mL of acetonitrile, under N₂, at room temperature. {1-[6-(trifluoromethyl)pyridin-3-yl]ethyl}(methyl)oxido-λ⁴-sulfanylidenecyanamide (2) is commonly known as sulfoxaflor and has the following structure

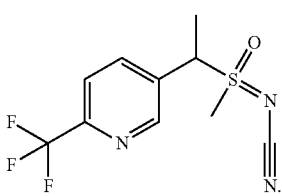

(2)

An exothermic output of about 8° C. was observed and the mixture became homogeneous as TFAA was added. After stirring at room temperature for 60 minutes, thin layer chromatography (TLC) analysis conducted with a 1:1 ratio of hexanes to acetone showed about a 2:1 ratio of compound (1) to compound (2). After 2 hours, TLC analysis under conditions indicated above showed only a minor amount of compound (2) remaining After stirring at room temperature for 3 hours, a white precipitate was present and the reaction mixture was filtered through a medium fritted funnel, washing with CH₃CN (acetonitrile). The resulting filtrate was then concentrated in vacuo. The post-vacuo residue was taken up in 30 mL of THF, and washed with two 10 mL volumes of saturated sodium thiosulfate and one 10 mL volume of saturated NaCl. The resulting organic phase was dried with Na₂SO₄/MgSO₄, filtered and concentrated in vacuo to give 0.82 g of a light yellow wax. The crude material was dissolved in acetone and chromatographed by flash chromatography using a Teledyne-Isco CombiFlash Companion® (Isco, Inc., Lincoln, Nebr.) flash chromatography system equipped with a 40 g RediSep silica gel column (Isco, Inc.). The chromatography was performed with a flow rate of 40 mL/minute, detection at 254 nm (monitored at 280 nm), and hexanes and acetone used as solvents. A linear gradient was used starting at 75% hexanes/25% acetone for two minutes and transitioning to 100% acetone over a period of 14 minutes and then held at 100% acetone for 8 minutes. Isolation of the major product gave 0.178 g (34% yield) of compound (1) as a light tan solid. ¹H NMR (DMSO-d₆) δ 8.58 (s, 1H), 8.03 (d, 1H, J=8.4), 7.61 (d, 1H, J=8.4), 5.22 (q, 1H, J=7.2), 3.38/3.46 (two singlets, 3H), 1.80 (d, 3H, J=7.2). MS: (ES⁺) 294 (M+H); (ES⁻) 292 (M−H).

Example 2

Preparation of [methyl(oxido){[1-oxido-6-(trifluoromethyl)pyridin-3-yl]methyl}-λ⁶-sulfanylidene] cyanamide (3)

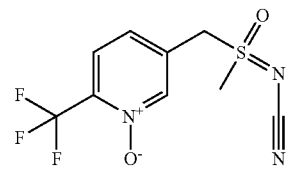

(3)

A 50 mL, three neck round bottom flask equipped with a magnetic stir bar and thermometer was charged with [(6-trifluoromethylpyridin-3-yl)methyl](methyl)oxido-λ⁴-sulfanylidenecyanamide (4), CH₂Cl₂ and urea hydrogen peroxide. [(6-trifluoromethylpyridin-3-yl)methyl](methyl)oxido-λ⁴-sulfanylidenecyanamide (4) has the following structure:

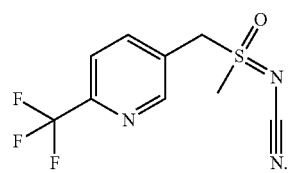

(4)

The resultant mixture was cooled in an ice bath to less than 5° C. and treated dropwise with trifluoroacetic anhydride (TFAA). An exothermic output of about 8° C. was observed as TFAA was added. After the mixture was kept for 60 minutes at 0-5° C., thin layer chromatography (TLC) analysis conducted with a 1:1 ratio of hexanes to acetone showed that compound (4) was mainly present. The reaction mixture was gradually allowed to warm to room temperature. After stirring at room temperature, TLC analysis was performed again and showed that compound (4) was mainly present. The reaction mixture was treated with 3 mL of anhydrous CH₃CN (acetonitrile) in an effort to dissolve insoluble material that was present in the reaction mixture. After about 3 hours, TLC analysis was performed again and showed a mixture of about a 3:1 ratio of compound (4) to what was assumed to be compound (3) given the presence of several minor products. After stirring at room temperature for 3 days, further TLC analysis indicated that none of compound 4 remained in the reaction mixture. In addition, there appeared to be a minor amount of compound (3) and a greater amount of a very polar material believed to be N-oxide-urea. The reaction mixture was filtered through a medium fitted funnel, washing with CH₂Cl₂ (dichloromethane). The resulting filtrate was concentrated in vacuo, diluted with 30 mL of THF and washed with two 10 mL volumes of saturated sodium thiosulfate. The resulting organic phase was dried with Na₂SO₄, filtered and concentrated in vacuo to give 1.33 g of a yellow oil. The crude material was dissolved in acetone and chromatographed by flash chromatography using a Teledyne-Isco CombiFlash Companion® (Isco, Inc., Lincoln, Nebr.) flash chromatography system equipped with a 40 g RediSep silica gel column (Isco, Inc.). The chromatography was performed with a flow rate of 40 mL/minute, detection at 280 nm (monitored at 254 nm), and hexanes and acetone used as solvents. A linear gradient was used starting at 75% hexanes/25% acetone for two minutes and transitioning to 100% acetone over a period of 14 minutes and then held at 100% acetone for 8 minutes. Isolation of compound (3) gave 75 mg (14% yield) of a light tan solid with the following properties: melting point: 201-203° C.; $^1$H NMR (DMSO-$d_6$) δ 8.48 (s, 1H), 8.00 (d, 1H, J=8.1), 7.52 (d, 1H, J=8.1), 4.63 (s, 2H), 3.02 (s, 3H); MS (ES$^-$) 278 (M−H).

Example 3

Preparation of 1-[methyl(oxido){1-[1-oxido-6-(trifluoromethyl)pyridin-3-yl]ethyl}-λ$^6$-sulfanylidene]urea (5)

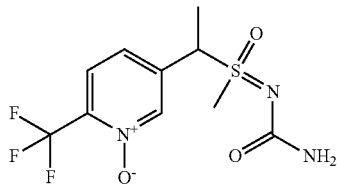

(5)

A mixture of compound (1) (the production of which is described in Example 1 above) in 5 mL of acetonitrile was treated with two drops of concentrated sulfuric acid. After stirring at room temperature for about 30 minutes, thin layer chromatography (TLC) analysis conducted with a 1:1 ratio of hexanes to acetone showed only compound (1) present in an aliquot diluted with a solution containing a 1:1 ratio of $CH_2Cl_2$ to MeOH. Two additional drops of concentrated sulfuric acid were then added to the reaction mixture. After about 3 hours, TLC analysis still mainly showed presence of compound (1). LC-MS showed a minor amount, about 7%, of a product with the correct mass for compound (5), but still about 85% of compound (1). The reaction mixture was then treated with 0.5 mL of $H_2O$ and three drops of concentrated sulfuric acid. After stirring at room temperature for about 21 hours, HPLC analysis showed no change in the reaction mixture. The reaction mixture, which had a turbid appearance at this stage, was treated with two more drops of concentrated sulfuric acid, warmed with a heat gun, and became homogenous. The mixture was then allowed to cool to room temperature. HPLC analysis was performed again and still mainly showed compound (1). The reaction mixture was then warmed with a heating mantle. After stirring at 70° C. for 4 hours, HPLC analysis indicated that all of compound (1) had been consumed and the presence of one major, more polar product. LC-MS showed a major product with the correct mass for compound (5). The reaction mixture was then concentrated under a stream of $N_2$, and the oil was taken up in warm $CH_3CN$ and blown multiple times to dryness. The residual dark yellow oil was dissolved in warm isopropanol and the solution placed in a refrigerator.

No crystals or solid had formed after 3 days in the refrigerator. The solvent was then removed with a stream of $N_2$ and the residue was dissolved in $CH_2Cl_2$ with a minor amount of methanol. The residue was then chromatographed by flash chromatography using a Teledyne-Isco CombiFlash Companion® (Isco, Inc., Lincoln, Nebr.) flash chromatography system equipped with a 12 g RediSep silica gel column (Isco, Inc.). The chromatography was performed with a flow rate of 30 mL/minute, detection at 254 nm, and dichloromethane and dichloromethane with 10% methanol were used as solvents. The following stepwise gradient was used: 100% dichloromethane for 2 minutes; 80% dichloromethane/20% dichloromethane/10% methanol for 2 minutes; 60% dichloromethane/40% dichloromethane/10% methanol for 2 minutes; 40% dichloromethane/60% dichloromethane/10% methanol for 2 minutes; 20% dichloromethane/80% dichloromethane/10% methanol for 2 minutes; and 100% dichloromethane/10% methanol for 4 minutes. Fractions containing the major product were combined and concentrated in vacuo to give 94 mg of a tan foam. $^1$H NMR (300 MHz, DMSO-d6) δ 8.53 (dd, J=4.1, 1.4 Hz, 1H), 7.97 (dd, J=8.4, 5.5 Hz, 1H), 7.61 (dd, J=8.5, 4.3 Hz, 1H), 6.36 (s, 1H), 6.11 (s, 1H), 4.99 (dq, J=13.9, 7.0 Hz, 1H), 3.22-3.08 (m, 3H), 1.73-1.67 (m, 3H). ESI MS (m/z) 312 [M+H]+.

Examples 4-7

Compounds (10), (11), (12) and (13) of Examples 4-7, respectively, are shown in Table I below. Compounds (6), (7), (8) and (9) (also shown in Table I below) were oxidized utilizing processes similar to those described above in connection with Examples 1 and 2 to provide compounds (10), (11), (12) and (13), respectively.

TABLE I

| Starting Compounds | Oxidized Compounds |
|---|---|
| (6) | (10) Found: $^1$H NMR (400 MHz, DMSO-d6, mixture of diasteriomers) 8.63-8.61 (m, 1H), 7.93-7.90 (m, 1H), 7.53-7.41 (m, 1H), 5.37-5.32 (m, 1H), 3.66 (s, 1.28H), 3.63 (s, 1.74H), 1.82-1.79 (m, 3H). ESI MS (m/z) 280 [M + H]+, 278 [M − H]−. |

TABLE I-continued

| Starting Compounds | Oxidized Compounds |
|---|---|
| 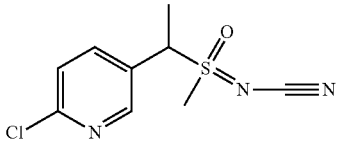<br>(7) | 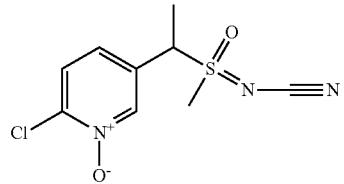 [SMILES: CC(c1ccc(Cl)[n+]([O-])c1)S(C)(=O)=NC#N]<br>(11)<br>Found: ¹H NMR (400 MHz, DMSO-d6, mixture of diasteriomers) δ 8.59 (d, J = 1.9 Hz, 1H), 7.90 (d, J = 8.5 Hz, 1H), 7.48 (dt, J = 8.6, 1.9 Hz, 1H), 5.16 (q, J = 7.1 Hz, 1H), 3.46 (s, 1.1H), 3.44 (s, 1.9H), 1.80 (d, J = 7.1 Hz, 3H). ESI MS (m/z) 261 [M + H]+, 258 [M − H]−. |
| 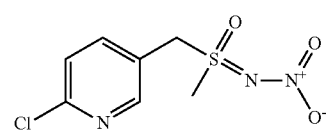<br>(8) | 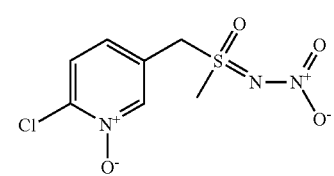 [SMILES: CS(=O)(Cc1ccc(Cl)[n+]([O-])c1)=N[N+](=O)[O-]]<br>(12)<br>Found: ¹H NMR (400 MHz, DMSO-d6) δ 8.54 (d, J = 1.8 Hz, 1H), 7.91 (d, J = 8.5 Hz, 1H), 7.41 (dd, J = 8.5, 1.8 Hz, 1H), 5.23 (d, J = 2.4 Hz, 2H), 3.62 (s, 3H). ESI MS (m/z) 268 [M + H]⁺, 264 [M − H]⁻. |
| 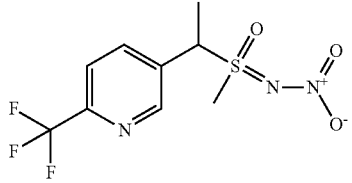<br>(9) | 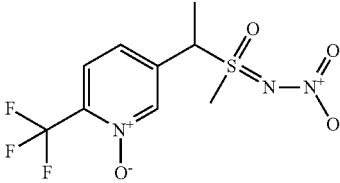<br>(13)<br>Found: ¹H NMR (400 MHz, DMSO-d6, mixture of diasteriomers) 8.63-8.61 (m, 1H), 8.08-8.05 (m, 1H), 7.68-7.63 (m, 1H), 5.43-5.39 (m, 1H), 3.71 (s, 1.4H), 3.67 (s, 1.6H), 1.99-1.82 (m, 3H). ESI MS (m/z) 314 [M + H]⁺, 312 [M − H]⁻. |

Examples 8-9

Compounds (14) and (15) of Examples 8-9, respectively, are shown in Table II below. Compounds (3) and (11) (also shown in Table II below) were acid hydrolyzed utilizing a process similar to that described above in connection with Example 3 to provide compounds (14) and (15), respectively.

TABLE II

| Starting Compounds | Acid Hydrolyzed Compounds |
|---|---|
| 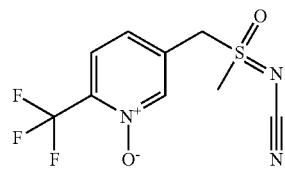<br>(3) | 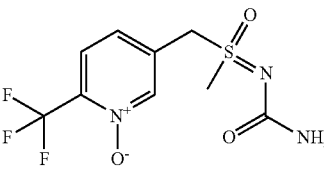<br>(14)<br>Found: ¹H NMR (300 MHz, DMSO-d6) δ 8.48 (d, J = 1.3 Hz, 1H), 8.00 (d, J = 8.3 Hz, 1H), 7.54 (dd, J = 8.2, 1.4 Hz, 1H), 6.40 (s, 1H), 6.18 (s, 1H), 4.93 (s, 2H), 3.14 (s, 3H). ESI MS (m/z) 298 [M + H]+. |

TABLE II-continued

| Starting Compounds | Acid Hydrolyzed Compounds |
|---|---|
| 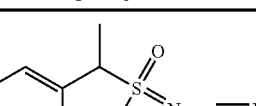<br>(11) | 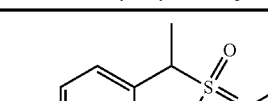<br>(15)<br>Found: $^1$H NMR (400 MHz, DMSO-d6, mixture of diasteriomers) 8.56-8.55 (m, 1H), 7.87-7.83 (m, 1H), 7.50-7.46 (m, 1H), 6.37 (bs, 1H), 6.08 (bs, 1H), 4.96-4.87 (m, 1H), 3.16 (s, 1.4H), 3.15 (s, 1.6H) 1.71-1.68 (m, 3H). ESI MS (m/z) 278 [M + H]$^+$. |

While the invention has been illustrated and described in detail in the foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A process for preparing an N-oxidized sulfoximine compound of formula (I)

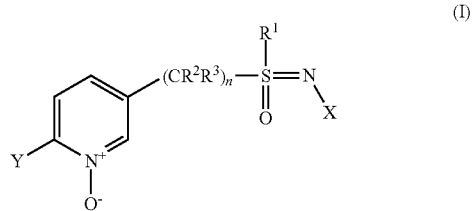

(I)

wherein
X represents $NO_2$, CN, $COOR^4$ or $CONH_2$;
$R^1$ represents ($C_1$-$C_4$) alkyl;
$R^2$ and $R^3$ individually represent hydrogen, methyl, ethyl, flouro, chloro or bromo;
n is an integer from 0-3;
Y represents ($C_1$-$C_4$) haloalkyl, F, Cl, Br, or I; and
$R^4$ represents ($C_1$-$C_3$) alkyl;
which includes performing an oxidation of a compound of formula (II)

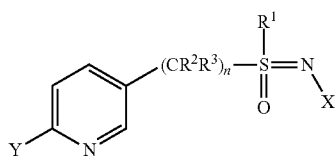

(II)

wherein X, $R^1$, $R^2$, $R^3$, n, Y and $R^4$ are as previously defined and the oxidation includes treating the compound of formula (II) with urea hydrogen peroxide and trifluoroacetic anhydride.

2. The process of claim 1, wherein X represents $NO_2$, CN or $CONH_2$.

3. The process of claim 1, wherein Y represents $CF_3$ or Cl.

4. The process of claim 1, wherein $R^2$ and $R^3$ independently represent hydrogen, methyl or ethyl.

5. The process of claim 1, wherein X, $R^2$, $R^3$, n, Y and $R^4$ are as previously defined, $R^1$ represents $CH_3$, n=1-3, the compound of formula (I) has the structure

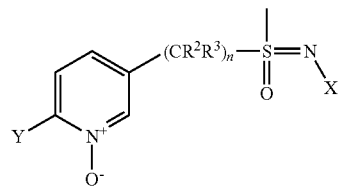

and the compound of formula (II) has the structure

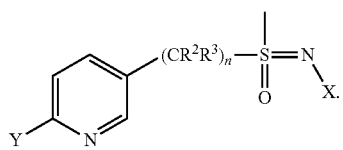

6. The process of claim 5, wherein X represents $NO_2$, CN or $CONH_2$, Y represents ($C_1$-$C_4$) haloalkyl, and $R^2$ and $R^3$ individually represent hydrogen, methyl, ethyl, flouro, chloro or bromo.

7. The process of claim 6, wherein X represents $NO_2$, CN or $CONH_2$, Y represents $CF_3$, and $R^2$ and $R^3$ individually represent hydrogen, methyl or ethyl.

8. A process for preparing an N-oxidized sulfoximine compound of formula (I)

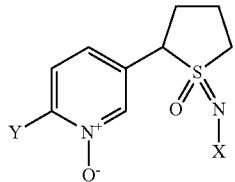

wherein
X represents $NO_2$, CN, $COOR^1$ or $CONH_2$;
Y represents ($C_1$-$C_4$) haloalkyl, F, Cl, Br, or I; and
$R^1$ represents ($C_1$-$C_4$) alkyl;
which includes performing an oxidation of a compound of formula (II)

wherein X, Y and $R^1$ are as previously defined and the oxidation includes treating the compound of formula (II) with urea hydrogen peroxide and trifluoroacetic anhydride.

9. The process of claim 1, which further includes conducting the oxidation in a polar solvent.

10. The process of claim 9, wherein the polar solvent is selected from the group consisting of dichloromethane, tetrahydrofuran, ethyl acetate, acetone, dimethylformamide, acetonitrile, and dimethyl sulfoxide.

* * * * *